| United States Patent [19] | [11] | 4,144,345 |
|---|---|---|
| Mrozik et al. | [45] | Mar. 13, 1979 |

[54] DIHYDROXYBENZISOXAZOLIN-3-YL-SUBSTITUTED-5-NITROIMIDAZOLES AS ANTIBACTERIALS AND ANTIPROTOZOALS

[75] Inventors: Helmut H. Mrozik, Matawan; Peter Kulsa, Plainfield, both of N.J.

[73] Assignee: Merck & Co., Inc., Rahway, N.J.

[21] Appl. No.: 867,552

[22] Filed: Jan. 6, 1978

Related U.S. Application Data

[63] Continuation-in-part of Ser. No. 855,861, Nov. 30, 1977, abandoned.

[51] Int. Cl.² .................. C07D 261/20; A61K 31/42
[52] U.S. Cl. ........................... 424/272; 260/307 DA; 548/339
[58] Field of Search ............... 260/307 DA; 424/272

[56] References Cited

U.S. PATENT DOCUMENTS 3,711,495    1/1973    Kulsa et al. ................ 260/307 D

OTHER PUBLICATIONS

Morrison et al–"Organic Chemstry"–Allyn & Bacon, Inc. (1959)–p. 651.

*Primary Examiner*—Raymond V. Rush
*Attorney, Agent, or Firm*—Walter Patton; Harry E. Westlake, Jr.

[57] ABSTRACT

Dihydroxybenzisoxazolin-3-yl-substituted-1-methyl-5-nitroimidazoles having the hydroxy- groups on adjacent 4,5-; 5,6- or 6,7-positions of the isoxazolin group. These compounds have antibacterial and antiprotozoal activity in humans and animals. They are particularly active against trypanosomiasis and trichomoniasis.

3 Claims, No Drawings

DIHYDROXYBENZISOXAZOLIN-3-YL-SUBSTITUTED-5-NITROIMIDAZOLES AS ANTIBACTERIALS AND ANTIPROTOZOALS

This application is a continuation-in-part of co-pending application U.S. Ser. No. 855,861, filed Nov. 30, 1977 and now abandoned.

SUMMARY OF THE INVENTION

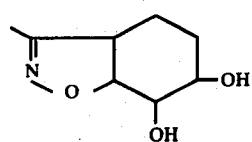

The novel compounds of the present invention are prepared by Scheme I:

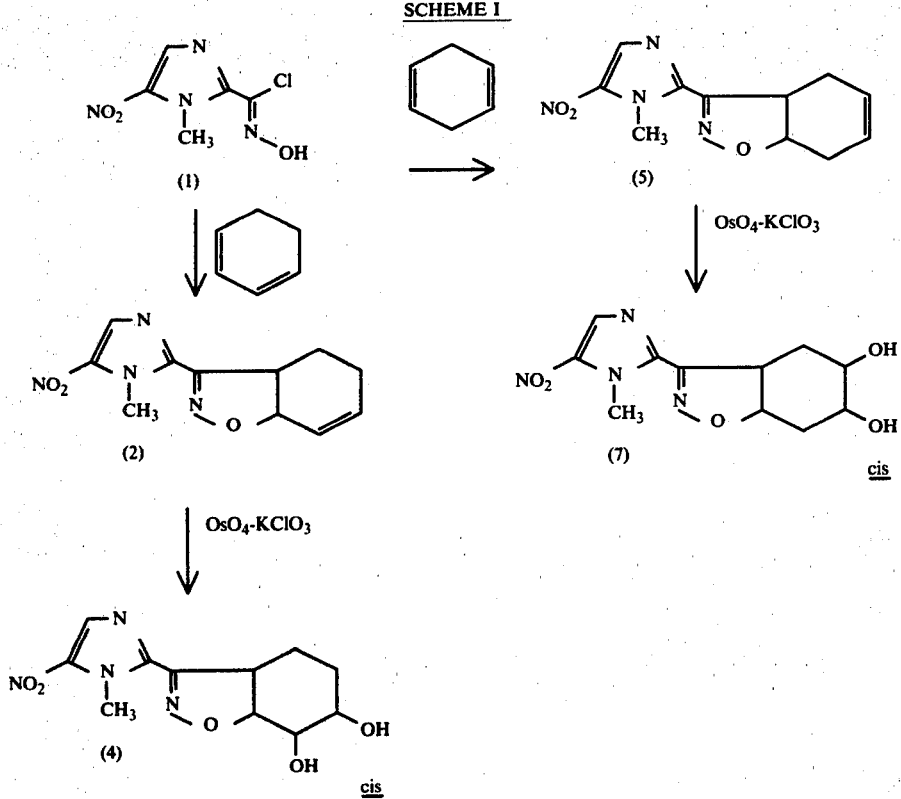

This invention relates to dihydroxybenzisoxazalin-3-yl-substituted-5-nitroimidazoles having the following structural formulas:

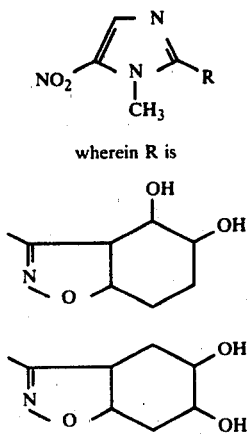

wherein R is

Intermediate 5 was prepared by a 1,3-dipolar addition of the readily available 1-methyl-5-nitroimidazol-2-hydroxamoyl chloride (1) and 1,4-cyclohexadiene. The 5,6-dehydro nitroimidazole derivative (5) was converted by $OsO_4$ catalyzed $KClO_3$ oxidation to the cis-5,6-diol (7), while oxidation with m-chloroperbenzoic acid (MCPBA) afforded an epoxide mixture which upon acid cleavage gave a mixture of trans-diols. Addition of the nitrile oxide (1) to 1,3-cyclohexadiene likewise gave in good yield a major dehydro nitroimidazole analog, characterized by NMR as the 6,7-dehydro compound (2). The minor product was identified as the 4,5-dehydro compound. The same chemical transformation as for the 5,6-isomer afforded a cis-6,7-diol (4) and a well defined epoxide leading to a mixture of trans-diols.

The hydroxamoyl chloride (1) is prepared from the 2-formyl-1-methyl-5-nitroimidazole following procedures known in the art. For example, reaction with hydroxylamine is followed by chlorination with nitrosyl chloride. Preparation of the 2-formyl starting material is described in U.S. Pat. No. 3,711,495 issued Jan. 16, 1973. The reaction of an olefin with the hydroxamoyl chloride is carried out in the presence of an organic base, such as triethylamine. An inert solvent system is used, for instance, tetrahydrofuran is suitable. The reaction takes place in from one-half to 2 hours at 0°–25° C.

The product is isolated by evaporating the solvent and purifying the residue by column chromatography.

The oxidation of the intermediates (2) and (5) are carried out in an inert solvent such as THF to which is added an aqueous solution of an oxidizing agent such as $KClO_4$ and a benzene solution of $OsO_4$. The reaction is usually complete in 1 to 6 hours at a temperature range of boiling solvent to room temperature.

The product is conveniently isolated by extracting the reaction mixture with an organic solvent, evaporating the solvent and purifying the residue by column chromatography.

The novel compounds of this invention have antibacterial and antiprotozoal activity especially against human and animal trypanosomiasis, including Chagas' disease, and trichomoniasis.

Trypanosomiasis is a term used to describe a group of allied protozoal diseases, each of which is due to infection with a species of the genus Trypanosoma.

The important trypanosomes pathogenic to domestic animals are *T. congolense*, *T. simiae*, *T. vivax*, and *T.brucei*. The latter trypanosome is morphologically identical to *T. gambiense*, responsible for human "sleeping sickness" of Africa. A trypanosome found in the Western Hemisphere is *T. cruzi*, which affects both domestic animals and man.

Acute Chagas' disease (*T. cruzi*) occurs predominantly in young children. The chronic form may be mild and asymptomatic, but complications from myocarditis and C.N.S. involvement may result with fatal outcome.

The compounds of this invention have particular value in the control of trypanosomiasis and trichomoniasis in domesticated animals, particularly cattle. For this purpose, they may be administered orally with an ingestible carrier as a component of the animals feedstuff, in the drinking water, in salt blocks and in unit dosage forms such as boluses and drenches. The amount of active ingredient required for optimum control of trypanosomiasis varies in accordance with such factors as the particular compound employed, the species of animals to be treated, the species of infecting parasite, the severity of infection, and whether the compound is employed therapeutically or prophylactically. In general, the novel compounds of the present invention when administered orally to domestic animals in daily doses of from about 0.1 mg. to about 500 mg. per kilogram of animal body weight are highly effective in controlling trypanosomiasis and trichomoniasis without intolerable toxic effect. When these compounds are to be employed as therapeutic agents, good results are obtained when the animals are fed a daily dose of from about 5 mg. to about 500 mg. and preferably 15 mg. to 250 mg. per kilogram of body weight.

The substituted imidazoles of the present invention may be administered, dispersed in or admixed with the normal elements of animals sustenance, i.e., the feed, drinking water or other liquids normally partaken by the animals. This method is preferred when it is desired to administer the active compounds continuously, either as a therapeutic or prophylactic agent, for a period of several days or more.

When the novel compounds of the present invention above are provided as a constituent of the feed, the required dosage may be supplied with feed compositions containing from about 0.0001 to 3 percent by weight of the active compound. Such medicated feed compositions can be prepared for direct use by mixing the above amount of active ingredient directly with the feed. The medicated feeds may also be prepared by the use of feed supplements containing a higher concentration of the active ingredient uniformly dispersed in a solid edible carrier such as corn meal, wheat shorts, alfalfa, etc. In general, feed supplements containing from about 5 percent to about 50 percent by weight of active ingredient may be satisfactorily employed to supply the desired dosage in the finished feed.

In the preparation of feed supplements, the active ingredient is added to the carrier and the whole mixed to give substantially uniform dispersion of the antitrypanosomiasis agent in the carrier.

When the substituted nitroimidazoles of this invention are used in the prevention and treatment of Chagas' disease and human "sleeping sickness," the compounds can be administered as intravenous, intramuscular, or interperitoneal injections suspended or dissolved in an inert non-toxic pharmaceutically acceptable carrier. When used as a prophylactic, 2–12 mg./kg. of body weight are injected every 1–8 months. The compounds can also be used orally against Chagas' disease or human "sleeping sickness." The oral dosage is 3–20 mg. per kg. twice a day for 5–10 days. This invention is more fully described in a reading of the following examples.

EXAMPLE 1

Preparation of 3-(1-Methyl-5-nitroimidazol-2-yl)-3a,4,5-7a-tetrahydro-1,2-benzisoxazole (2)

A THF solution (250 ml.) containing 1-methyl-5-nitroimidazol-2-hydroxamic acid chloride (1) (10.23 g., 0.05 mole) and 1,3-cyclohexadiene (16.03 g., 0.2 mole) was stirred in an ice bath. A solution of triethylamine (5.05 g., 0.05 mole, 6.97 ml.) in THF (125 ml.) was added slowly during 2 hours. Stirring continued for 1 hour at ice bath temperature. Then the mixture was allowed to come to 25° C. and was allowed to stand at this temperature overnight. The reaction mixture was concentrated in vacuo at 50° C. to afford an oily residue (12.4 g.) which was dissolved in $HCCl_3$ and purified on a column of silica gel (360 g., E. Merck silica gel 60) prepared in $HCCl_3$. Fractions 13 to 52 (100 ml., $HCCl_3$) show one spot in TLC [$SiO_2$, benzene-EtOAc, (9:1) $R_f$ 0.6] and were combined to yield 11.7 g. (94%) crystalline 3-(1-methyl-5-nitroimidazol-2-yl)-3a,4,5,7a-tetrahydro-1,2-benzisoxazole, melting point 137°–139° C.

Elemental analysis ($C_{11}H_{12}N_4O_3$): Calculated: C, 53.22; H, 4.87; N, 22.57. Found: C, 53.22; H, 4.83; N, 22.56.

EXAMPLE 1a

Preparation of 3-(1-Methyl-5-nitroimidazole-2-yl)-3a,6,7,7a-tetrahydro-1,2-benzisoxazole Fractions number 55 through 69 of Example 1 contain the 4,5-double bond isomer of that compound, which is isolated by careful repeated chromatography on a 1000μ silica-gel plate (20 × 20 cm.) and identified by its NMR spectrum.

EXAMPLE 2

Preparation of
2-(3a,4,5,6,7,7a-Hexahydro-6,7-oxido-1,2-benzisoxazol-3-yl)-1-methyl-5-nitroimidazole (3)

A solution of 3-(1-methyl-5-nitroimidazol-2-yl)-3a,4,5,7a-tetrahydro-1,2-benzisoxazole (0.90 g., 3.6 mmole), m-chloroperbenzoic acid (1.8 g. of 85% material, 8.8 mmole) in $HCCl_3$ (50 ml.) was kept 48 hours at 25° C. The reaction mixture was washed with aqueous $Na_2CO_3$, $H_2O$, dried (anhydrous $MgSO_4$) and concentrated in vacuo. Crystallization from acetone-ether gave 420 mg. (44%) of 2-(3a,4,-5,6,7,7a-hexahydro-6,7-oxido-1,2-benzisoxazol-3-yl)-1-methyl-5-nitroimidazole, m.p. 144°–70° C. Recrystallized from acetone-ether gave m.p. 150°–151° C.

Elemental analysis ($C_{11}H_{12}N_4O_4$): Calculated: C, 50.00; H, 4.58; N, 21.20. Found: C, 49.88; H, 4.48; N, 21.68.

EXAMPLE 3

Preparation of
6,7-Cis-Dihydroxy-3a,4,5,6,7,7a-hexahydro-3-(1-methyl-5-nitroimidazol-2-yl)-1,2-benzisoxoazol (4)

To a solution of 3-(1-methyl-5-nitroimidazol-2-yl)-3a,4,5,7a-tetrahydro-1,2-benzisoxazole (5.30 g., 21.4 mmole) in THF (385 ml.) stirred in an oil bath of 50° C. was added in rapid succession an aqueous solution of $KClO_3$ (3.58 g., 29.2 mmole) in 190 ml. of water and $OsO_4$ (1.1 mmole, 2.8 ml. of 10% (w/v) $OsO_4$ in $C_6H_6$). The reaction temperature was maintained with vigorous stirring for 3 hours, when TLC ($SiO_2$, ethyl acetate) indicated completion of the reaction. The mixture was poured into water (500 ml.) and extracted with ethyl acetate (3 × 250 ml.). The organic phases were combined, washed with saturate aqueous sodium chloride solution, dried (anhydrous $MgSO_4$) and concentrated in vacuo. The residue was purified on a column of $SiO_2$ (700 g., E. Merck silica gel 60) in ethyl acetate solution to give 3.3 g. crude 6,7-cis-dihydroxy-3a,4,5,6,7,7a-hexahydro-3-(1-methyl-5-nitroimidazol-2-yl)-1,2-benzisoxoazol, crystallized from ethyl acetate-ether to yield 2.8 g. (46%) (4), m.p. 157°–159° C.

Elemental analysis ($C_{11}H_{14}N_4O_5$): Calculated: C, 46.81; H, 5.08; N, 19.85. Found: C, 46.64; H, 4.91; N, 19.68.

EXAMPLE 3a

Preparation of
4,5-Cis-Dihydroxy-3a,4,5,6,7,7a-hexahydro-3-(1-methyl-5-nitroimidazol-2-yl)-1,2-benzisoxazole Following the procedure of Example 3 using 3-(1-methyl-5-nitroimidazole-2-yl)-3a,6,7,7a-tetrahydro-1,2-benzisoxazole in place of 3-(1-methyl-5-nitroimidazole-2-yl)-3a,4,5,7a-tetrahydro-1,2-benzisoxazole, there is obtained 4,5-cis-dihydroxy-3a,4,5,6,7,7a-hexahydro-3-(1-methyl-5-nitroimidazol-2-yl)-1,2-benzisoxazole.

EXAMPLE 4

Preparation of
3-(1-Methyl-5-nitroimidazol-2-yl)-3a,4,7,7a-tetrahydro-1,2-benzisoxazole (5)

A mixture of (1) (2.05 g., 0.01 mole), 1,4-cyclohexadiene (3.2 g., 0.04 mole) in toluene (100 ml.) was stirred under reflux for 3 hours, filtered hot and let cool to 25° C. The filtrate was concentrated in vacuo, the residue dissolved in $HCCl_3$ and chromatographed on $SiO_2$ (E. Merck, silica gel 60) to give 3-(1-methyl-5-nitroimidazol-2-yl)-3a,4,7,7a-tetrahydro-1,2-benzisoxazole as a light oil 0.917 g. (37%) which solidified, m.p. 123°–126° C. It was recrystallized from acetone-ether, m.p. 126°–128° C.

Elemental analysis ($C_{11}H_{12}N_4O_3$): Calculated: C, 53.22; H, 4.87; N, 22.57. Found: C, 53.53; H, 5.08; N, 22.36.

EXAMPLE 5

Preparation of
2-(3a,4,5,6,7,7a-Hexahydro-5,6-oxido-1,2-benzisoxazol-3-yl)-1-methyl-5-nitroimidazole (6)

A solution of 3-(1-methyl-5-nitroimidazol-2-yl)-3a,4,7,7a-tetrahydro-1,2-benzisoxazole (90 mg., 0.40 mmole), 3-$ClC_6H_4CO_3H$ (180 mg., 0.88 mole) in $HCCl_3$ (4 ml.) was stirred 16 hours at 25° C. Workup with methylene chloride, saturated aqueous sodium bicarbonate and water and recrystallization from acetone-ether gave 44 mg. 2-(3a,4,5,6,7,7a-hexahydro-5,6-oxido-1,2-benzisoxazol-3-yl)-1-methyl-5-nitroimidazole, m.p. 171°–173° C. TLC showed one major and one minor spot, (after recrystallization TLC showed only one spot).

Elemental analysis ($C_{11}H_{12}N_4O_4$): Calculated: C, 50.00; H, 4.58; N, 21.20. Found: C, 50.28; H, 4.71; N, 21.11.

EXAMPLE 6

Preparation of
5,6-cis-Dihydroxy-3a,4,5,6,7,7a-hexahydro-3-(1-methyl-5-nitroimidazol-2-yl)-1,2-benzisoxazole (7)

Reaction of 3-(1-methyl-5-nitroimidazol-2-yl)-3a,4,7,7a-tetrahydro-1,2-benzisoxazole (248 mg., 1.0 mmole) with $KClO_3$ (166 mg., 1.36 mmole, dissolved in 9 ml. of water) and $OsO_4$ (0.13 ml., 13 mg. 0.05 mmole of 10% solution in $C_6H_6$) in THF (18 ml.) is carried out for 3 hours at 50° C. Workup with water-ethyl acetate and recrystallization from ethyl acetate yielded 135 mg. 5,6-cis-dihydroxy-3a,4,5,6,7,7a-hexahydro-3-(1-methyl-5-nitroimidazol-2-yl)-1,2-benzisoxazole, m.p. 190°–192° C.

Elemental analysis ($C_{11}H_{14}N_4O_5$): Calculated: C, 46.81; H, 5.08; N, 19.85. Found: C, 46.81; H, 5.02; N, 19.53.

EXAMPLE 7

Preparation of
6,7-trans-Dihydroxy-3a,4,5,6,7,7a-hexahydro-3-(1-methyl-5-nitroimidazol-2-yl)-1,2-benzisoxazole A solution of 2-(3a,4,5,6,7,7a-hexahydro-6,7-oxido-1,2-benzisoxazol-3-yl)-1-methyl-5-nitroimidazole (132 mg., 0.5 mmole) in tetrahydrofuran (11 ml.) is stirred at 18° C. while perchloric acid (1.2 ml., 23% aqueous $HClO_4$) is added dropwise. The reaction mixture is kept for 2 hours at 18° C., then diluted with $HCCl_3$, washed with aqueous $NaHCO_3$ - solution and evaporated in vacuo to a pink glass, the major compound of which is identified by NMR and mass spectra as 6,7-trans-dihydroxy-3a,4,5,6,7,7a-hexahydro-3-(1-methyl-5-nitroimidazol-2-yl)-1,2-benzisoxazole.

EXAMPLE 7a

Preparation of 5,6-trans-Dihydroxy-3a,4,5,6,7,7,a-hexahydro-3-(1-methyl-5-nitroimidazol-2-yl)-1,2-benzisoxazole Following the procedure of Example 7 using 2-(3a,4,5,6,7,7a-hexahydro-5,6-oxido-1,2-benzisoxazol-3-yl)-1-methyl-5-nitroimidazole in place of 2-(3a,4,5,6,7,,7a-hexahydro-6,7-oxido-1,2-benzisoxazol-3-yl)-1-methyl-5-nitroimidazole, one obtains 5,6-trans-dihydroxy-3a,4,5,6,7,7,a-hexahydro-3-(1-methyl-5-nitroimidazol-2-yl)-1,2-benzisoxazole.

What is claimed is:

1. The compound having the structural formula:

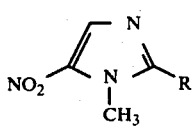

wherein R is

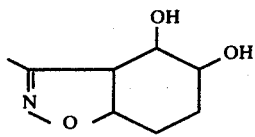

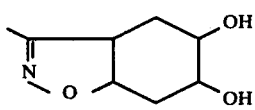

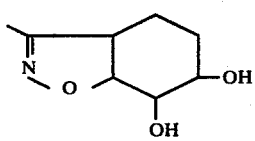

and non-toxic pharmaceutically acceptable salts thereof.

2. A compound according to claim 1 having the structural formula:

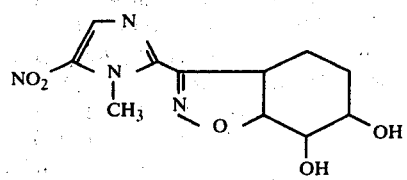

and non-toxic pharmaceutically acceptable salts thereof.

3. A composition for the treatment of trypanosomiasis comprising an inert carrier and an effective amount of a compound having the structure:

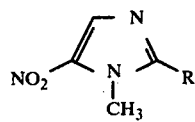

wherein R is

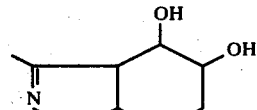

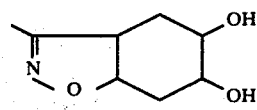

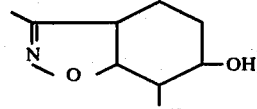

and the non-toxic, pharmaceutically acceptable salts thereof.

* * * * *